United States Patent [19]

Leeds

[11] Patent Number: 4,466,956
[45] Date of Patent: Aug. 21, 1984

[54] METHOD OF THERAPY FOR ORAL HERPES SIMPLEX

[76] Inventor: Robert Leeds, 9425 S.W. 142 St., Miami, Fla. 33176

[21] Appl. No.: 553,489

[22] Filed: Nov. 21, 1983

Related U.S. Application Data

[63] Continuation-in-part of Ser. No. 315,911, Oct. 28, 1981, abandoned.

[51] Int. Cl.³ .................... A61K 31/79; A61K 33/18
[52] U.S. Cl. .................................... 424/80; 424/150; 424/240
[58] Field of Search .................... 424/150, 80, 240

[56] References Cited

PUBLICATIONS

Merck Manual, 10th Ed., 1961, pp. 1441–1444.
Handbook of Nonprescription Drugs, 5th Ed., 1977, p. 305.
Chemical Abstracts 79:13803J (1973).
Chemical Abstracts 83:188782x (1975).
Chemical Abstracts 83:188271e (1975).

Primary Examiner—Leonard Schenkman
Attorney, Agent, or Firm—Robert J. Van Der Wall

[57] ABSTRACT

There is disclosed a method for the treatment of oral herpes simplex that manifests itself as ulcerations and ulcers of the type that appear in or near the mouth or other mucous membranes or other such conditions as canker sores, cold sores, fever blisters, aptheous ulcerations and the like. Said method comprises the serial application of povidone-iodine and then application immediately thereafter of triamcinolone acetonide used as an anti-inflammatory agent and adhesive. The foregoing serial treatment is preferably repeated on a once or twice per day basis for two or more days and it results in a highly accelerated relief of paint in a matter of minutes or hours, and complete elimination of the ulceration in a matter of a week or less.

10 Claims, No Drawings

METHOD OF THERAPY FOR ORAL HERPES SIMPLEX

CROSS-REFERENCE TO RELATED APPLICATION

This application is a continuation-in-part of U.S. application Ser. No. 315,911, filed Oct. 28, 1981 now abandoned.

FIELD OF THE INVENTION

The present invention relates to the field of a method of therapy of a condition known as oral herpes simplex which manifests itself as an ulceration of the type that appear in or near the mouth or in other mucous membrances, including such conditions as canker sores, cold sores, fever blisters and the like. The invention is particularly directed to a method for treating same using serial application of two compositions of matter to eliminate the ulceration and to relieve pain suffered by the patient much sooner than is available with conventional therapy, the inventive method using compositions of matter for which contraindication is suggested by the prior art.

BACKGROUND OF THE INVENTION

A condition known as oral herpes simplex manifests itself as ulcerations and ulcers of the type that appear in the mouth or other mucous membranes. Similar conditions such as canker sores, cold sores, fever blisters and the like produce pain in the affected areas, which is believed caused by viral infections. These conditions generally persist for a period of twelve to fourteen days if untreated and produce considerable discomfort for the patient during most of that period. The pain and persistence of the condition can be reduced somewhat with usual anti-microbial agents, but there is no method known to Applicant involving serial application of two compositions of matter as therapy for this condition nor any technique for the treatment of this condition which results in relief of pain generally in a matter for minutes, and where the affected area occurs on the lip, results in virtual elimination of the pain after the first treatment.

Prior art has included treatment utilizing the commercially available campho-phenique which is manufactured by Winthrop Chemical, the application of a lotion known as Dalidyne available from Dalin Pharmaceuticals, utilized as a treatment for the oral cavity, Polydine, available from Century Pharmaceuticals which may be used in the oral cavity only if not swallowed. Prepodyne swabs, a polozamer iodine solution available from West Chemical and povidone-iodine compositions not used in combination with serial application of another composition as in the subject invention, and available under the well known registered trademark Betadine from the Purdue Frederick Company.

Also, corticosteriods such as triamcinolone acetonide dental paste available from Squibb as Kenalog in Orabase is sometimes used for temporary relief of pain and other symptoms associated with oral inflammation and ulcerative lesions, but because this preparation is a corticosteriod, its use is contraindicated in the presence of fungal, viral or bacterial infections of the mouth or throat, and thus is contraindicated for use with herpes simplex in the prior art.

Synthetic corticosteriods offer a marked anti-inflammatory action, and one of them, Kenalog-40 Injection, also available from Squibb is listed as a treatment for bullous dermatitis herpetiformis, but such preparations modify the body's immune responses to the stimula. Similarly the natural corticosteriod Orabase HCA, available from Hoyte Laboratories is contraindicated for fungal, viral or bacterial infections of the oral mucosa, with the manufacturer pointing out that the defensive responses of the oral tissues are depressed by corticosteriod therapy, possibly resulting in virulent strains of oral microorganisms multiplying without producing the usual warning symptoms of infection. Thus, generally speaking, the use of corticosteriods is contraindicated by the prior art in the treatment of ulcerations called herpes simplex and ulcers of the type that appear in or near the mouth or other mucous membranes as well as such conditions as canker sores, cold sores, fever blisters and the like.

SUMMARY OF THE INVENTION

Bearing in mind the foregoing, it is a principal object of the present invention to provide a method for the prompt and effective treatment of the aforesaid conditions and, in particular, the pain symptoms associated therewith.

A further object of the invention is to provide comprising the serial application of two compositions of matter which in combination produce the anti-microbial effects of one composition and the anti-inflammatory and adhesive qualities of a second composition in combination.

A related object of the invention is to overcome the contraindication of an anti-inflammatory agent by the serial applications thereof in combination with an anti-microbial agent.

A further object of the invention is to effect relief of pain symptoms associated with the above-described conditions in a much shorter time than has been demonstrated with prior art therapy.

One more object of the invention is to provide a basis for inventive activity in the form of research and clinical studies and of seeking a therapy for herpes II, the venereal disease.

Other objects and advantages will become apparent to those who are skilled in the art upon reading the following description of the invention.

In accordance with the invention there is provided a method for the treatment of oral herpes simplex that manifests itself as ulcerations and ulcers of the type that appear in or near the mouth or other mucous membranes and other such conditions as canker sores, cold sores, fever blisters and the like which comprises the serial application of two medications. The first of these medications is an anti-microbial agent, the chemical povidone-iodine, which may optionally contain a tincture of myrrh. The second medication is applied immediately thereafter and is a corticosteriod, generally a synthetic corticosteriod, of which the preferred embodiment is triamcinolone acetonide. The latter medication is generally in a dilute solution, the preferred commercially available material being known as Kenalog in Orabase from Squibb which is physically in the form of a paste. The latter medication acts as an adhesive in the oral cavity, in addition to its well-known anti-inflammatory effects. The combination is then allowed to remain on the affected area and the treatment is repeated preferably four to eight times over a period of three or four days. It is contemplated that serial treatment may be accomplished more than once daily.

In the inventor's experience this method relieves pain and causes disappearance of what is presently believed to be an ulceration caused by viral infection in the affected areas. The method results in the relief of pain generally in a matter of minutes, and where the affected area occurs on the lip, the return of pain is uncommon there after the first treatment. The affected areas dry up in a period of about three days after initial application, frequently disappearing altogether in a period of seven days, which compares favorably with a customary untreated period of recovery of twelve to fourteen days, and results in the relief of pain much sooner and more effectively than prior art therapy.

DETAILED DESCRIPTION

In the preferred embodiment, the condition known as oral herpes simplex or herpes simplex I is to be treated by serial application of two compositions of matter and a repitition of said treatment one or two times per day for a period of three or four days.

The affected area has applied to it initially the chemical povidone-iodine, such as Betadine from the Purdue Frederick Company, which constitutes anti-microbial therapy. The chemical formulation of Betadine is apparently one hundred percent active ingredient povidone-iodine, there being no solvent or other constituents listed in the Physician's Desk Reference. The povidone-iodine is therefore applied in a one hundred percent concentration, because the method of the present invention does not require dilution thereof. The quantity to be applied is, of course, dependent upon the size of the ulceration, the medication being applied to cover the ulceration and overlap the adjoining skin area only to a slight degree.

Immediately thereafter the corticosteriod, triamcinolone acetonide, such as Kenalog in Orabase from Squibb, is also applied to the affected area without removal of the Betadine. The chemical formulation for Kenalog in Orabase is that each gram thereof provides 1 mg. (0.1%) triamcinolone acetonide in emollient dental paste containing gelatin pectin and sodium carboxymethylcellulose in a polyethylene and mineral oil gel base. The amount applied is also controlled by the size of the ulceration and is a similar quantity to the previously applied Betadine. The medications are allowed to remain on the affected area, with Kenalog in Orabase acting as an adhesive as well as an anti-inflammatory therapy.

At least several hours later, and preferably on the same date, the foregoing medications are repeated in the same manner, with the povidone-iodine medication being applied before the triamcinolene acetonide. The serial treatment of preferably two applications per day is then repeated daily for the next three or four days, although application twice per day is not necessarily required. The period of treatment depends, of course, on the persistence of the condition and pain and varies with the patient.

The affected areas generally dry up in a period of about three days after the initial application, frequently disappearing in a period of seven days. Relief of pain is usually quite rapid and can be immediately after the first treatment when the affected area is on the lip.

Having described the presently preferred embodiment of the invention, the advantages and objects of the invention will be apparent to those skilled in the art and reasonable modifications thereto are fully contemplated herein without departing from the true spirit of the invention. Accordingly, there are covered all alternatives, modifications, and equivalents as may be included within the spirit and scope of the invention as defined solely by the appended claims.

What is claimed is:

1. The method of therapy for oral herpes simplex comprising:
    application to and covering of an affected area with povidone-iodine; and
    immediate application to and covering of the same area with diluted triamcinolone acetonide.

2. The method which further comprises a first repetition of the method of claim 1.

3. The method which comprises utilization of the method of claim 1 at least once per day.

4. The method which further comprises use of the method of claim 3 on at least two days in proximity to each other.

5. A method of therapy for oral herpes simplex comprising:
    application to and covering of an affected area with povidone-iodine; and
    immediate application to and covering of the same area with a diluted concentration of triamcinolone acetonide in an emollient dental paste.

6. The method of claim 5 wherein the diluted concentration is 0.1 percent.

7. The method of claim 5 wherein the diluted concentration of triamcinolone acetonide in an emollient dental paste is Kenalog in Orabase.

8. The method which further comprises a first repetition of the method of claim 5.

9. The method which further comprises utilization of the method of claim 8 on at least two days in proximity to each other.

10. The method of claim 5 wherein the povidone-iodine is Betadine.

* * * * *